United States Patent [19]

Crawford et al.

[11] Patent Number: 5,104,800

[45] Date of Patent: Apr. 14, 1992

[54] ONE-STEP CEPHALOSPORIN C AMIDASE ENZYME

[75] Inventors: Mark S. Crawford, Bothell; David B. Finkelstein; John A. Rambosek, both of Seattle, all of Wash.

[73] Assignee: Merck & Co., Inc., Rahway, N.J.

[21] Appl. No.: 372,399

[22] Filed: Jun. 27, 1989

[51] Int. Cl.$^5$ .......................... C12N 9/78; C12N 9/80; C12N 9/89; C12P 35/00

[52] U.S. Cl. .................................. 435/227; 435/224; 435/230; 435/47

[58] Field of Search .................. 435/51, 47, 172.3, 195, 435/228, 227, 230, 832, 837, 49

[56] References Cited

U.S. PATENT DOCUMENTS

| | | | |
|---|---|---|---|
| 3,144,395 | 8/1964 | Murao | 435/51 |
| 3,239,394 | 3/1966 | Walton | 435/51 |
| 3,522,250 | 7/1970 | Kerwin et al. | 435/51 |
| 3,749,641 | 7/1973 | Takahashi et al. | 435/51 |
| 3,801,458 | 4/1974 | Flides et al. | 435/51 |
| 3,821,081 | 6/1974 | Abe | 435/51 |
| 3,880,713 | 4/1975 | Fleming et al. | 435/51 |
| 3,915,798 | 10/1975 | Yamaguchi et al. | 435/47 |
| 3,930,949 | 1/1976 | Kutzbach et al. | 435/51 |
| 3,945,888 | 3/1976 | Takahashi et al. | 435/51 |
| 3,960,662 | 6/1976 | Matsuda et al. | 435/47 |
| 3,962,036 | 6/1976 | Liersch | 435/51 |
| 4,141,790 | 2/1979 | Niwa et al. | 435/51 |
| 4,774,179 | 9/1988 | Ichikawa et al. | 435/51 |

FOREIGN PATENT DOCUMENTS

| | | |
|---|---|---|
| 780676 | 9/1972 | Belgium . |
| 321849 | 6/1984 | European Pat. Off. . |
| 0275901 | 7/1988 | European Pat. Off. . |
| 3447023 | 6/1986 | Fed. Rep. of Germany . |
| 2241557 | 4/1975 | France . |
| 50-107186 | 2/1975 | Japan . |
| 52-082791 | 3/1977 | Japan . |
| 52-143289 | 6/1977 | Japan . |
| 52-128293 | 10/1977 | Japan . |
| 53-86094 | 3/1978 | Japan . |
| 53-94093 | 8/1978 | Japan . |
| 54-110394 | 8/1979 | Japan . |
| 56-85298 | 7/1981 | Japan . |
| 58-190399 | 5/1983 | Japan . |
| 0110292 | 6/1985 | Japan . |
| 60-110292 | 6/1985 | Japan . |
| 61-21097 | 1/1986 | Japan . |
| 61-152286 | 7/1986 | Japan . |
| 63-74488 | 8/1988 | Japan . |
| 2142336 | 1/1985 | United Kingdom . |

OTHER PUBLICATIONS

Dev. Ind. Microbiol., 5, 349 (1964).
Agric. Biol. Chem. 45, 1561-67, (1981).
Process Biochem., 11, 21 (1976).
DNA 3: 479-488 (1984).
DNA 5: 219-225 (1986).
J. Mol. Biol. 186, 547-555 (1985).
Gene 29: 21-26 (1984).
Molec. Gen. Genet., 168, 111-115 (1979).
J. Bact. 142, 508-512 (1980).
Journal of Bacteriology, Dec. 1987, pp. 5815-5820, vol. 169.
Journal of Bacteriology, Sep. 1985, pp. 1222-1228, vol. 163.
Applied and Environmental Microbiology, Nov. 1988, pp. 2603-2607, vol. 154, No11.

Primary Examiner—Douglas W. Robinson
Assistant Examiner—Irene Marx
Attorney, Agent, or Firm—Raymond M. Speer; Hesna J. Pfeiffer

[57] ABSTRACT

A process for the one-step conversion of cephalosporin C and derivatives thereof to the corresponding 7-aminocephalosporanic acid and derivatives comprising treating said cephalosporin C and derivatives with a cephalosporin C amidase enzyme of a recited sequence, the DNA encoding said enzyme, and expression thereof in a suitable host, e.g., Bacillus species under the control of a suitable promoter.

1 Claim, No Drawings

ONE-STEP CEPHALOSPORIN C AMIDASE ENZYME

BRIEF SUMMARY OF THE INVENTION

The present invention relates to an improved process for the one-step conversion of cephalosporin C and derivatives thereof to the corresponding 7-aminocephalosporanic acid (7-ACA) and derivatives comprising treating said cephalosporin C and derivatives with a cephalosporin C amidase enzyme of a recited sequence, the DNA encoding said enzyme, and expression thereof in a suitable host, e.g., Bacillus species under the control of a suibtable promoter.

The present invention further relates to an enzyme, cephalosporin C amidase, having the specific amino acid sequence and physical/chemical characteristics set forth further below, as well as to any subunit thereof which is enzymatically active as a one-step cephalosporin C amidase.

The present invention still further relates to the DNA fragment encoding an enzyme, cephalosporin C amidase, having the nucleotide base sequence capable of expressing said enzyme, set forth further below.

The present invention also relates to expression of the DNA fragment, i.e., the gene encoding an enzyme, cephalosporin C amidase, in any suitable prokaryotic or eukaryotic host, especially in species of the genus Bacillus, more especially in Bacillus megaterium and Bacillus subtilis. This is accomplished, as explained in more detail further below, by cloning the gene coding for cephalosporin C amidase activity from a particular strain of B. megaterium, fusing it to a promoter sequence, e.g., a strong constitutive promoter, and transforming the resulting construction into the desired host, e.g., B. subtilis and B. megaterium, which are maintained in an appropriate culture medium. Cephalosporin C amidase activity is monitored and harvesting of the enzyme is carried out by conventional means.

BACKGROUND OF THE INVENTION

The present invention is in the field of enzymatic cleavage (deacylation), especially one-step cleavage of the 7-aminoadipoyl side chain (also referred to as 7-α-aminoadipyl) of cephalosporin C. Since the 7-aminoadipoyl side chain is removed by cleavege of an amide linkage, the particular enzyme which accomplishes the conversion is referred to herein as an amidase. Cephalosporin C itself is a fermentation product which is the starting point for nearly all currently marketed cephalosporins. However, synthetic manipulation to produce these various commercial cephalosporins basically starts with the 7-aminocephalosporanic acid, which must be derived from the cephalosporin C by cleavage of the 7-aminoadipoyl side chain.

Currently, the method of choice in the art for cleaving the 7-aminoadipoyl side chain is chemical. the basic imino-halide process requires blocking of the amino and carboxyl groups on the 7-aminoadipoyls side chain, and several methods for accomplishing this are currently used. However, as presently employed, the chemical cleavage process has serious disadvantages. Among these are the requirements of a multi-step and complex process, extremely low operating temperatures, expensive reagents, significant quantities of process by-products resulting in effluent treatment problems, and purification of a highly impure starting material before chemical treatment begins. Consequently, there has been an ongoing search for a microbiological or fermentative process which would achieve enzymatic deacylation of cephalosporin C to provide 7-aminocephalosporanic acid on a more economic basis than the chemical process currently in use.

However, this search for a successful microbiological process has largely proved futile, certainly with respect to one of commercial scale. This is a result of the particular characteristics of the aminoadipoyl side chain of the cephalosporin C molecule, since, by contrast, penicillin G, which has a phenylacetyl side chain, has been successfully deacylated by enzymatic cleavage using penicillin acylase produced by a variety of microorganisms. Reports of successful one-step enzymatic deacylation of cephalosporin C in the literature, on the other hand, are often unreproducible or provide only very marginal yields.

Moreover, no person to date has succeeded in isolating and sequencing an enzyme from the genus Bacillus, cephalosporin C amidase, which can achieve one-step cleavage of the aminoadipoyl side chain of cephalosporin C. Nor, has anyone isolated and sequenced the gene which encodes the cephalosporin C amidase enzyme, or succeeded in expressing that gene in a prokaryotic host.

A summary of the literature which describes these ongoing efforts to achieve enzymatic cleavage of cephalosporin C is set out below.

1. One-Step Enzymatic Deacylation: Ceph C → 7-ACA

| | |
|---|---|
| Dev. Ind. Microbiol., 5, 349 (1964) | Achromobacter, |
| U.S. Pat. No. 3,239,394 | Brevibacterium, |
| (Merck) | Flavobacterium |
| Soil enrichment method | |
| of screening and selecting | |
| for microorganisms | |
| Jap. Pat. Pub. 53-94093 (1978) | Pseudomonas sp. BN-188 |
| (Meiji) | |
| Jap. Pat. Pub. 52-143289 (1977) | Aspergillus sp. |
| U.S. Pat. No. 4,141,790 | Alternaria sp. |
| (Meiji) | |
| U.S. Pat. No. 4,774,179 (1988) | Pseudomonas |
| Jap. Pat. Pub. 61-21097 (1986) | sp. SE-83 and SE-495 |
| Jap. Pat. Pub. 61-152286 (1986) | |
| (Asahi) | |
| Fr. Pat. 2,241,557 (1975) | Bacillus cereus |
| (Aries) | var. fluorescens |
| Jap. Pat. Pub. 52-082791 (1977) | Bacillus megaterium |
| (Toyo Jozo) | NRRL B 5385 |
| N-(N'-phenylthiocarbamyl)- | |
| cephalosporin C → 7-ACA | |
| Ger. Pat. 3,447,023 (1986) | Bacillus licheniformis |
| (Hoechst) | |
| In the presence of α-keto | |
| acids, enzyme is D-amino acid | |
| transaminase | |
| EP-A- 0 321 849 | Pseudomonas, |
| (Hoechst) | Bacillus subtilis, |
| | Anthrobacter parafineus |
| γ-glutamyl transpeptidase | |

2. One-Step Enzymatic Deacylation: Penicillin G → 6-APA

| | |
|---|---|
| Jap. Pat. Pub. 58-190399 (1983) | Bacillus megaterium |
| (Shionogi) | var. penicilliticum |
| | ATCC 14945 |
| U.S. Pat. No. 3,144,395 (1964) | Bacillus megaterium |
| (Olin Mathieson) | var. penicilliticum |
| | ATCC 14945 |
| Br. Pat. Pub. 2,142,336A (1985) | Bacillus megaterium |
| (Squibb) | |
| Applied and Environmental (1988) | Anthrobacter viscosus |
| Microbiology, 54, 2603-2607 | E. coli |
| (Banyu) | Pseudomonas |
| Penicillin acylase | |
| α-subunit specificity | |
| genetic sequence | |

3. Two-Step Enzymatic Deacylation: Ceph C → 7-ACA

| | |
|---|---|
| U.S. Pat. No. 3,960,662 (1976) Agric. Biol. Chem. 45, 1561-67 (1981) (Toyo Jozo) Deamination with D-amino acid oxidase followed by deacylation EP-A- 0 275 901-A2(1988) (Hoechst) | Pseudomonas sp. |
| i) Ceph C → Gl-7-ACA* [U.S. Pat. No. 3,801,458 (1974) (Glaxo)] | Trigonopsis variabilis |
| ii) Gl-7-ACA* → 7-ACA gamma-glutamyl-transpeptidase | Pseudomonas Anthrobacter parafineus Bacillus subtilis |
| 4. Enzymatic Deacylation: Gl-7-ACA* → 7-ACA | |
| Jap. Pat. Pub. 52-128293 (1977) 53-86094 (1978) (Banyu) | Bacillus, Anthrobacter, Alcaligenes |
| 5. Enzymatic Deacylation: Other → 7-ACA | |
| a) Phenoxy- and Phenylacetyl 7-ADCA → 7-ADCA | |
| U.S. Pat. No. 3,821,081 (1974) Process Biochem., 11, 21 (1976) (Toyo Jozo) | Bacillus megaterium |
| U.S. Pat. No. 3,749,641 (1973) (Takeda) | 61 different genera |
| U.S. Pat. No. 3,915,798 (1975) Belg. Pat. No. 780,676 (Toyo Jozo) | Anthrobacter simplex Kluyvera citrophila Proteus rettgeri Bacillus megaterium |
| b) Phenoxy-7-ADCA → 7-ADCA | |
| U.S. Pat. No. 3,880,713 (1975) (Glaxo) | Erwinia aroideae |
| c) Cephalothin → 7-ACA | |
| U.S. Pat. No. 3,522,250 (1970) (American Home Products) | Escherichia coli |
| d) Various cephalosporins → 7-ACA | |
| U.S. Pat. No. 3,930,949 (1976) (Bayer) penicillin acylase | E. coli |
| U.S. Pat. No. 3,962,036 (1976) (Ciba-Geigy) | E. coli, Bacillus megaterium, subtilis, Micrococcus roseus, lysodeikticus |
| 3-lower alkoxy-7-acyl cephalosporins; microorganisms possessing acylase activity | Alcaligenes faecalis, Aerobacter cloacae, Fusarium avenaceum, semitectum, Emericellopsis minima, Penicillium chrysogenum, Aspergillus ochraceus, Trichophyton mentagrophytes, Epidermophyton floccosum, Streptomyces lavendulae |
| Jap. Pat. Pub. 50-107186 (1975) (Toyo Brewing) | Anthrobacter, Bacillus, Escherichia, |
| phenylacetamido 7-ACA derivatives are deacylated | Kluyvera, Micrococcus, Nocardia, Proteus, Xanthomonas |
| 6. Enzymatic Acylation: 7-ACA → Other | |
| U.S. Pat. No. 3,945,888 (1976) (Takeda) | E. coli, Bacillus, Proteus, |
| 7-ACA → cephalosporins | Pseudomonas |
| Jap. Pat. Pub. 54-110394 (1979) (Banyu) | Anthrobacter viscosus |
| 7-ACA → cephapirin | |
| 7. One-Step-Recombinant: Ceph C → 7-ACA | |
| Jap. Pat. Pub. 60-110292 (1985) (Asahi) Recombinant E. coli with gene from Comamonas sp. SY-77-1; one-step conversion | Comamonas |
| Jap. Pat. Pub. 61-152286 (1986) (Asahi) Recombinant E. coli with gene from Pseudomonas sp. SE83; | Pseudomonas |
| genetic sequences described and claimed one step process already claimed in U.S. Pat. No. 4,774,179 | |
| Jap. Pat. Pub. 63-74488 (1988) (Asahi) Recombinant E. coli expression of D-amino acid oxidase and GL-7-ACA* acylase construct | Trigonopsis variabilis, Comamonas |

GL-7-ACA = glutaryl 7-ACA = 3-acetoxymethyl-7-β-(4-carboxybutanamido)-ceph-3-em-4-carboxylic acid.

DETAILED DESCRIPTION OF THE INVENTION

In accordance with the present invention there is provided a process for the one-step conversion of cephalosporin C and derivatives thereof of the formula:

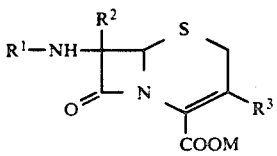

(I.)

where
R$^1$ is

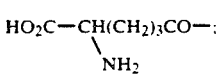

R$^2$ is —H;
R$^3$ is —H or

of CH$_2$R$^4$, where R$^4$ is —H, —OH, or

and M is $^-$; —H; alkali metal or other pharmaceutically acceptable salt; pharmaceutically acceptable ester; or readily removable carboxyl covering group;
to a 7-aminocephalosporanic acid of the formula:

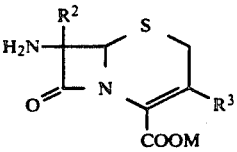

(II.)

where R$^2$, R$^3$, and M are as defined above; comprising: treating a compound of Formula I with an enzyme, cephalosporin C amidase, capable of converting a compound of Formula I to a compound of Formula II in one step; said enzyme comprising the following primary translation product amino acid sequence or a post-translational modification thereof:

```
  1  MKFIKSFILV  TFSFFCMITP  AFASVPGVDK
                 SMGRGATKGI  VSVSHPLAAE  AGIKILKQGG

61  NAVDAAAAIQ  LSLNVVEPMM  SGIGGGGFIM
                 IYNKKENKIT  MLDSREMAPQ  NVTPELFLDG

121  KGKPIPFSKR  HTTGKAVGVP  GTLKGVETAL
                 EKYGTLDISQ  VIDPAIKQAE  KGVKVNWITA

181  QYIDENVKKL  QNNQAAANVF  VPNGQPLKEG
                 DTLVQPDLAK  TLKLIKKQGS  EVFYSGQIGK

241  ALTKEVQKRE  GTMTTEDLEN  YVVKEREPIR
                 SEYRGYELAG  AASPSSGSLT  VQQILELMEG

301  FDVQKMGANS  PEYLHYLTEA  MHLAFADRAA
                 YMADEDFYDV  PTKGLLDEDY  IKERRKIINP

361  NRSTADVKEG  DPWKYEGTEP  TSMKKVKEEK
                 TPIGQTTHFS  VMDKWGNMVA  YTTTIEQVFG

421  SGIMVPDYGF  MLNNEMTDFD  ATPGGVNQVE
                 PGKRPRSSMS  PTFVLKDGNP  FMAIGSPGGA

481  THASVSETI  MNVLDHQMLI  QDAILAPRIY
                 SAGYPTVRWE  PGIEQNTRLE  LMGKGHVYEE

541  KPQHIGNVQA  VIFDYEKGKM  YGGADNTREG
                 TVQGVYNVSY  KSKKPKEIKE  EKKGPFTLKV

601  NGAVYPYTAE  QMKLINEKPY  IQSDKLLLGL
                 GVIGTGDLET  FRPDKKSYLP  VIKVAKSLGY

661  KAKWNEKDKE  ALLEKDPADI  EDPEDDGSVT
                 IIFHSKFKFH  MVDNTLRDEE  FEVIVVLTLN

721  EC
``` wherein, for the above sequence, the following amino acid abbreviations are employed:
Ala=A; Arg=R; Asn=N; Asp=D; Cys=C; Gln=Q; Glu=E; Gly=G; His=H; Ile=I; Leu=L; Lys=K; Met=M; Phe=F; Pro=P; Ser=S; Thr=T; Trp=W; Try=Y; Val=V.

In accordance with the present invention, there is also provided an enzyme, cephalosporin C amidase, capable of one-step cleavage of the aminoadipoyl side chain of cephalosporin C to give 7-ACA, and having the primary translation product amino acid sequence recited in the paragraph immediately above and any post-translational modification thereof, and having the physical/chemical characteristics described in detail further below.

In accordance with the present invention there is further provided the purified, isolated and sequenced DNA fragment, i.e., the gene encoding an enzyme, cephalosporin C amidase, having the amino acid sequence recited in the paragraph further above. The nucleotide base sequence of the gene is set out further below, as are the nucleotide bases of the regulatory sequences which precede and follow the sequence of the gen itself. This gen was isolated from a particular strain of Bacillus megaterium which was found to have cephalosporin C amidase activity in accordance with assays described further below.

In accordance with the present invention there is still further provided a method of expressing the cephalosporin C amidase enzyme having the amino acid sequence set out further above in a suitable prokaryotic or eukaryotic host, e.g., Bacillus species by fusing the gene sequence encoding the enzyme to a promoter sequence, e.g., a strong constitutive promoter sequence, cloning the resulting construction into an appropriate vector, and transforming said vector into said suitable host. Details of this method are set out further below.

Vectors containing the construction of fused gene and 141/142 promoter sequences described further below, transformed into a *Bacillus megaterium* and a *B. subtilis* host, have been deposited with the American type Culture Collection (ATCC), 12301 Parklawn Drive, Rockville, Md. 20852, and have been assigned deposit numbers 68024 and 68023, respectively.

The One-Step Enzymatic Cleavage Process

With reference to the compounds of Formula I above, the group $R^1$ defines the moiety $$HO_2C-\underset{NH_2}{\underset{|}{CH}}(CH_2)_3CO-$$

which is the cephalosporin C 7-aminoadipoyl side chain.

For the group "M", the expression "readily removable carboxyl covering group" means a conventional substitutent which takes the place of the hydrogen of the carboxyl group and thereby prevents said group from reacting with any reagents employed in any subsequent synthesis. Such covering of the carboxyl group is often necessary to prevent unwanted competing reactions involving said groups from taking place. The conventional covering substituent must also be "readily removable", by which is meant that it is selectively removable, i.e., it is not likely to be removed during the course of ordinary procedures which are to be carried out on the cephalosporin nucleus and side chains, while, on the other hand, it is likely to be removed by procedures which are not so harsh as to disturb the basic ring structure of the cephaloporin nucleus or unprotected substituents thereon.

It will also be noted that for M=H in Formula II, at physiological pH an internal zwitterion is formed by the groups $NH_3^+$ and $COO^-$, so that M, in that case, is actually $-$, indicating an anion.

The group $R^3$ is defined to include various substituents characteristic of typical fermentation products, e.g., for cephalosporin C, $R^3$ would be $CH_2R^4$ where $R^4$ is $$-O\overset{O}{\underset{||}{C}}CH_3.$$

It is contemplated that none of the substituents defining $R_3$ would in any way interfere with the enzymatic action of the cephalosporin C amidase of the present invention, largely for the reasons discussed above.

The group $R^3$ is defined to include various substituents characteristic of typical fermentation products, e.g., for cephalosporin C, $R^3$ would be $CH_2R^4$ where $R^4$ is $$-O\overset{O}{\underset{||}{C}}CH_3.$$

It is contemplated that none of the substituents defining $R_3$ would in any way interfere with the enzymatic action of the cephalosporin C amidase of the present invention, largely for the reasons discussed above.

Thus, in accordance with the method of the present invention, desacetoxycephalosporin C ($R^3 = CH_2R^4$ where $R^4 = H$) may be converted to 7-aminodesacetoxycephalosporanic acid (7-ADCA) to an extent essentially equivalent to the conversion of cephalosporin C to 7-aminocephalosporanic acid (7-ACA). This results from the fact that the functional group at the 3-position is not crucial to the binding of substrate to the enzyme.

The process of one-step enzymatic conversion of cephalosporin C and derivatives to 7-aminocephalosporanic acid and derivatives with which the present invention is concerned may be schematically represented as follows:

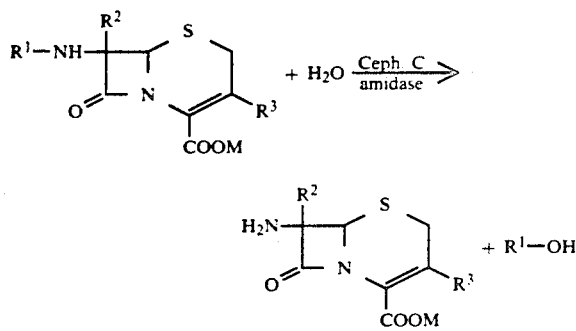

More particularly, the conversion of cephalosporin C to 7-aminocephalosporanic acid may be illustrated as follows:

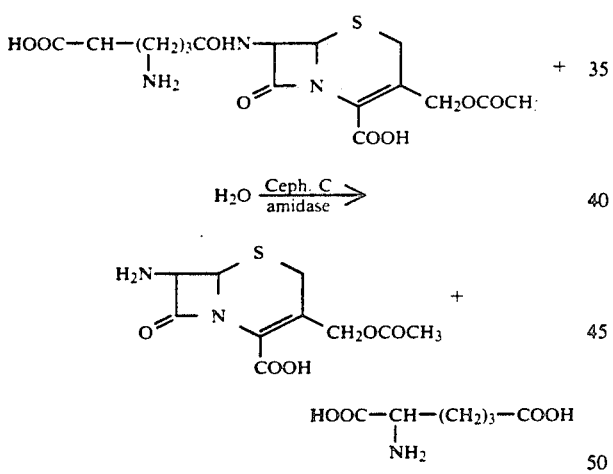

The process of the present invention may be carried out in any way which effectively brings the cephalosporin C amidase of the present invention into contact with the compounds of Formula I so that enzymatic conversion of these compounds to the compounds of Formula II can take place. This is the definition of the term "treating" in its broadest context. Ordinarily, it would be preferred to employ a cell free broth of crude cephalosporin C or derivative as the feed stream and treat it in a batch-wise fashion with crude cephalosporin C amidase broth. This approach realizes the greatest efficiencies since it does not require any substantial purification of the reactants initially. Of course, modifications are possible. E.g., the reactants may be purified to whatever extent desired before being brought into contact with each other. Also, it would be possible to carry out the process in a continuous manner rather than batch-wise. The contacting of the reactants themselves may be modified in various ways in keeping with advances in process technology. Thus, an immobilized enzyme column may be employed for the cephalosporin C amidase with the compound of Formula I being passed through the column. Another example of such process technology is that relating to membrane reactors. The preferred method of contacting the reactants is by way of the immobilized enzyme column.

Further below working examples describe the method currently employed to demonstrate the enzymatic deacylation of cephalosporin C, which involves a preliminary purification of the cephalosporin C amidase, largely for the purpose of increasing the concentration of enzyme and thus promoting the production of higher amounts of 7-aminocephalosporanic acid. Consequently, the method in the working examples would not necessarily be suggestive of methods which would be utilized for commercial production.

The Cephalosporin C Amidase Enzyme

The primary translation product, or precursor, which gives rise to the cephalosporin C amidase enzyme of the present invention comprises 722 amino acids, beginning with methionine (Met) and ending with cysteine (Cys), the sequence for which is set out further above. The primary translation product is processed, i.e., modified by the producing host, to yield an active enzyme consisting essentially of two subunits, the beginning amino acid sequences of which are underlined in the overall sequence as follows:

| | | | | | |
|---|---|---|---|---|---|
| 1 MKFIKSFILV | TFSFFCMITP | AFA<u>SVPGVDK</u> | <u>SMGRGATKGI</u> | <u>VSVSHPLAAE</u> | <u>AGIKILKQGG</u> |
| 61 NAVDAAAAIQ | LSLNVVEPMM | SGIGGGGFIM | IYNKKENKIT | MLDSREMAPQ | NVTPELFLDG |
| 121 KGKPIPFSKR | HTTGKAVGVP | GTLKGVETAL | EKYGTLDISQ | VIDPAIKQAE | KGVKVNWITA |
| 181 QYIDENVKKL | QNNQAAANVF | VPNGQPLKEG | DTLVQPDLAK | TLKLIKKQGS | EVFYSGQIGK |
| 241 ALTKEVQKRE | GTMTTEDLEN | YVVKEREPIR | SEYRGYELAG | AASPSSGSLT | VQQILELMEG |
| 301 FDVQKMGANS | PEYLHYLTEA | MHLAFADRAA | YMADEDFYDV | PTKGLLDEDY | IKERRKIINP |
| 361 NRSTADVKEG | DPWKYEGTEP | TSMKKVKEEK | TPIGQ<u>TTHFS</u> | <u>VMDKWGNMVA</u> | <u>YTTTIEQVFG</u> |
| 421 SGIMVPDYGF | MLNNEMTDFD | ATPGGVNQVE | PGKRPRSSMS | PTFVLKDGNP | FMAIGSPGGA |
| 481 TIIASVSETI | MNVLDHQMLI | QDAILAPRIY | SAGYPTVRWE | PGIEQNTRLE | LMGKGHVYEE |
| 541 KPQHIGNVQA | VIFDYEKGKM | YGGADNTREG | TVQGVYNVSY | KSKKPKEIKE | EKKGPFTLKV |
| 601 NGAVYPYTAE | QMKLINEKPY | IQSDKLLLGL | GVIGTGDLET | FRPDKKSYLP | VIKVAKSLGY |
| 661 KAKWNEKDKE | ALLEKDPADI | EDPEDDGSVT | IIFHSKFKFH | MVDNTLRDEE | FEVIVVLTLN |
| 721 EC | | | | | |

The gene product, i.e., the primary translation product comprising 722 amino acids, is a part of the present invention to the extent that it is enzymatically active as described herein. Also, as noted above, enzymatically active subunits thereof, particularly post-translational modifications which inherently result in enzymatic activity, are included. Other, artifical changes are also possible. Predictably, smaller subunits of the cephalosporin C amidase enzyme of the present invention, or different conformations of that same enzyme, will retain the full enzymatic activity of the enzyme whose sequence is recited herein. These forms of the amidase enzyme of the present invention are the full functional equivalents thereof and are thus contemplated to be a part of the present invention. These forms are sometimes referred to as microheterogeneous forms, since they are a single gene product, i.e., a protein produced from a single gene unit of DNA, which is structurally modified following translation. It is possible, using techniques well known to a biochemist, to effect various changes in the cephalosporin C amidase enzyme of the present invention, and then evaluate its enzymatic activity as a cephalosporin C amidase quickly and efficiently using the assays described further below. Such well-known techniques include acetylation at the N-terminus, glycosylation, phosphorylation, and proteolysis. Proteolysis may include exoproteolysis wherein one or more terminal amino acids are sequentially, enzymatically cleaved to produce microheterogeneous forms which have fewer amino acids than the original gene product. Proteolysis may also include endoproteolytic modification that results from the action of endoproteases which cleave the peptide at specific locations within the amino acid sequence. Similar modifications can occur during the purification process which may result in the production of microheterogeneous forms. The most common modification occurring during purification is proteolysis, which is, however, generally held to a minimum by the use of protease inhibitors.

As is well known, the biochemical action of an enzyme is determined not only by its amino acid sequence, but by its overall conformation as well. Moreover, the conformation of an enzyme is subject to environmentally induced changes, e.g., by pH, temperature, solvent systems, culture media, ionic factors, and the like. To the extent that such environmentally induced conformational changes in the the enzyme do not result in loss of cephalosporin C amidase activity, the various conformations of the enzyme are a part of the present invention.

The amino acid sequence of the cephalosporin C amidase enzyme of the present invention, recited further above, was deduced by DNA sequence analysis of the gene coding for the enzyme, and the accuracy of the results have been verified by sequencing three independent isolates from three different strains of *Bacillus megaterium*. However, since 100% accuracy cannot be totally assured, it has been considered desirable to also identify the cephalosporin C amidase enzyme of the present invention in terms of a number of physical and chemical attributes which it uniquely has. Purification of the enzyme for which such data has been derived is explained in more detail further below. Those data are set out in the following table:

A. Structural

1. Apparent MW: 126,000 by gel filtration
2. Subunit MW (by SDS PAGE): Alpha (large): 45 kd; Beta (small): 37 kd
3. Stoichiometry: alpha (2) beta (2) oligomer (MW approximately 165 kd)
4. Specific activity: 1–3 $\mu$mol 7-ACA/mg enzyme/hr (increases as enzyme is diluted)

B. Kinetic

1. Temperature optimum: 37°–40° C.
2. pH optimum: 7–8
3. Stable pH range: 5.0–8.0
4. Activity stimulated by 10–15% (w/v) ammonium sulfate
5. Km: 1.3 mM cephalosporin C amidase [Km with glutaryl-4-aminobenzoate (GAB) approximately M but with 20-fold higher turnover number]
6. Substrate specificity: DAC>Ceph C>DAOC 12.5%, 9.1%, 2.3%, (% 7-ACA production at 3 h) [DAC=desacetylcephlosporin C; DAOC=desacetoxycephalosporin C]

C. Inhibitors

1. NOT inhibited by PenG or 6-APA
2. Potent inhibitors (>90% inhibition at 10 mM):
   Glycine         L-alanine
   Glutamate       D-alanine
   Glutamine

The Gene Encoding the Enzyme

The gene encoding the primary translation product cephalosporin C amidase enzyme of the present invention contains 722 codons, which correspond to the 722 amino acids of the primary translation product enzyme. The precise sequence of codons is set forth further below and for the gene itself begins with nucleotide base 1 and ends with base 2166, in the numbering system employed to set forth the sequence. The sequence of nucleotide bases (codons) which precede the gene sequence, bases −163 through −1, and the sequence of bases (codons) which follow the gene sequence, nucleotide bases 2167 through 2370, contain regulatory sequences of the gene within the *Bacillus megaterium* cell from which the gene was isolated. The preceding sequence contains, for example, a promoter sequence and a ribosome binding site. While these additional sequences are not a part of the gene itself, they are, nevertheless, a part of the present invention, since they potentially play a role in efficient transcription of the gene in the prokaryotic host Bacillus species. The entire sequence of nucleotide bases is shown in compact form in the following table:

| | | | | | | |
|---|---|---|---|---|---|---|
| −163 ATAGTAGAGA | GTACATCACG | CACATTCCAT | CTGGTAATAG | TGAAGTAGTC | GAATCCTGTA |
| −103 ACAGCCCTTT | GTGAATTTGT | GAAGATCAGT | AAAAGTTTCA | TTAGTTATTG | CATTTGTTTT |
| −43 TAGAAACAAT | GGATCTATAA | TCATTTTGAA | AGGAGACTAA | TTTATGAAAT | TTATAAAAAG |
| 18 TTTTATTTTA | GTTACTTTCA | GTTTCTTTTG | TATGATTACA | CCGGCTTTTG | CAAGTGTCCC |
| 78 TGGAGTGGAT | AAGTCAATGG | GAAGGGGAGC | AACCAAAGGA | ATCGTATCAG | TTTCTCATCC |
| 138 GTTAGCTGCT | GAGGCAGGTA | TAAAAATATT | AAAACAAGGT | GGAAATGCAG | TCGATGCAGC |
| 198 AGCTGCCATT | CAATTATCGT | TAAATGTAGT | TGAGCCAATG | ATGTCTGGAA | TTGGCGGCGG |

-continued

| | | | | | | |
|---|---|---|---|---|---|---|
| 258 TGGTTTTATC | ATGATTTATA | ATAAAAAGGA | AAATAAAATA | ACGATGCTCG | ATAGCCGCGA | |
| 318 AATGGCCCCG | CAAAATGTAA | CGCCTGAACT | TTTTTTAGAT | GGAAAAGGAA | AACCAATTCC | |
| 378 TTTTAGTAAG | CGTCACACTA | CTGGAAAAGC | AGTAGGAGTT | CCAGGAACGT | TAAAGGGTGT | |
| 438 CGAAACAGCT | CTTGAGAAAT | ATGGAACGTT | GGATATATCT | CAAGTAATAG | ATCCAGCAAT | |
| 498 TAAACAAGCA | GAAAAGGGG | TTAAAGTCAA | TTGGATCACT | GCTCAATATA | TCGATGAAAA | |
| 558 TGTAAAAAAA | CTTCAAAATA | ATCAAGCTGC | AGCAAATGTG | TTTGTTCCTA | ACGGCCAACC | |
| 618 CTTGAAAGAG | GGAGATACCC | TCGTTCAACC | AGATCTGGCA | AAGACGCTGA | AATTAATTAA | |
| 678 AAAACAAGGA | TCGGAAGTAT | TTTATAGTGG | CCAAATTGGT | AAAGCACTTA | CCAAAGAAGT | |
| 738 GCAAAAACGC | GAAGGAACAA | TGACAACAGA | GGATTTAGAG | AATTATGTGG | TGAAAGAAAG | |
| 798 AGAACCGATT | AGATCGGAAT | ATAGAGGATA | CGAATTGGCA | GGGGCAGCTT | CACCAAGTTC | |
| 858 AGGCAGCTTG | ACTGTCCAAC | AAATCCTAGA | GCTAATGGAA | GGATTCGATG | TACAAAAGAT | |
| 918 GGGGGCGAAC | TCCCCTGAAT | ATCTTCATTA | TCTGACCGAA | GCCATGCATC | TAGCTTTTGC | |
| 978 CGATCGCGCT | GCCTATATGG | CAGATGAAGA | TTTTTATGAT | GTACCAACAA | AAGGACTATT | |
| 1038 GGATGAAGAT | TATATAAAAG | AAAGAAGAAA | AATCATTAAT | CCAAATAGAT | CAACGGCTGA | |
| 1098 TGTAAAAGAA | GGCGATCCAT | GGAAGTATGA | GGGCACAGAA | CCCACTTCAA | TGAAGAAGGT | |
| 1158 AAAAGAAGAG | AAAACTCCGA | TCGGACAAAC | GACTCACTTT | TCTGTCATGG | ATAAGTGGGG | |
| 1218 AAATATGGTT | GCTTATACGA | CTACAATCGA | GCAAGTATTC | GGATCAGGTA | TCATGGTACC | |
| 1278 TGATTATGGA | TTCATGCTTA | ATAATGAAAT | GACGGATTTT | GATGCGACTC | CCGGTGGCGT | |
| 1338 TAACCAAGTA | GAGCCAGGAA | AAAGACCGAG | AAGCAGTATG | TCCCCGACCT | TCGTATTAAA | |
| 1398 AGATGGTAAT | CCCTTCATGG | CCATTGGTTC | ACCAGGCGGG | GCGACGATAA | TCGCATCGGT | |
| 1458 ATCTGAAACG | ATTATGAATG | TGCTTGACCA | TCAAATGCTA | ATTCAAGATG | CGATACTTGC | |
| 1518 GCCACGTATT | TATTCTGCTG | GTTATCCGAC | TGTTAGATGG | GAACCGGGAA | TTGAACAAAA | |
| 1578 TACAAGGTTG | GAGTTAATGG | GCAAAGGCCA | TGTTTATGAA | GAAAAACCCC | AACATATCGG | |
| 1638 AAATGTGCAA | GCTGTTATTT | TTGATTATGA | AAAGGGGAAA | ATGTATGGAG | GAGCCGACAA | |
| 1698 TACGAGAAAA | GGAACTGTTC | AAGGAGTGTA | TAATGTATCC | TATAAATCGA | AAAAACCAAA | |
| 1758 AGAAATAAAA | GAAGAAAAGA | AGGGACCGTT | TACCTTAAAA | GTGAATGGAG | CCGTTTATCC | |
| 1818 TTATACAGCT | GAACAAATGA | AACTGATAAA | TGAAAAACCC | TATATCCAAT | CAGACAAATT | |
| 1878 GCTACTTGGT | TTGGGTGTAA | TTGGAACCGG | GGACTTAGAA | ACATTTAGAC | CAGATAAAAA | |
| 1938 ATCGTACTTA | CCGGTGATAA | AAGTAGGCAA | ATCATTAGGA | TATAAAGCAA | AATGGAACGA | |
| 1998 AAAAGATAAA | GAGGCACTAT | TGGAAAAAGA | TCCGGCGGAT | ATTGAAGATC | CCGAAGATGA | |
| 2058 TGGTAGTGTT | ACGATTATTT | TTCACTCTAA | GTTTAAGTTC | CATATGGTTG | ATAATACCCT | |
| 2118 GAGAGACGAA | GAGTTTGAAG | TGATAGTAGT | CTTAACCCTA | AATGAATGTT | AATAATTCCC | |
| 2178 CTTTTGCTAT | GTGCATAAGG | GGCCAATTAT | TTTTTTGGAA | ATGATAGCTA | AAAAGATTGG | |
| 2238 ACATTTTTCT | ATGAAGCATT | CGGTGCAAGG | CTCATCTTAT | ATCGCTGATA | AACCCAGATA | |
| 2298 GTACTACCAA | GCCAAAACCC | ACCTGTGAAA | AAGTCCCCAA | GGTTGTCACT | TGGGAACTGT | |
| 2358 GCACCCAATC | AAAA | | | | | |

In addition to the specific sequence of nucleotide bases set out above, the cephalosporin C amidase gene of the present invention is also uniquely characterized by the points at which various endonucleases, i.e., restriction enzymes, cut the gene. These are summarized in the following chart, where all of the enzymes shown have a recognition sequence six bases or more long:

```
               1       400      800     1200     1600     2000
           ----+--------+--------+--------+--------+--------+--------
     Bal I ----+--------+-----°--+--------+----°---+--------+--------
     Bgl I ----+--------+--------+----°---+--------+--------+--------
     Bgl II----+--------+-----°--+--------+--------+--------+--------
     Cla I ----+--------+--°-----+--------+--------+--------+--------
     Eco B ----+--------+--------+--------+--------+-----°--+--------
     Eco B ----+--°-----+--------+--------+--------+--------+--------
     EcoP 15---+----°---+--------+--------+--------+--------+--------
     EcoP 15---+-°------+--------+--------+-----°--+--------+--------
     Hpa I ----+--------+--------+--------+--°-----+--------+--------
     Kpn I ----+--------+--------+--------+--°-----+--------+--------
     Nco I ----+--------+--------+--------+--°-----+--------+--------
     Nde I ----+--------+--------+--------+--------+--------+--°-----
     Nsi I ----+--------+--------+----°---+--------+--------+--------
     Pst I ----+--------+--°-----+--------+--------+--------+--------
     Pvu I ----+--------+--------+----°---°+--------+--------+--------
     Pvu II----+---°----+--------+--------+--------+-----°--+--------
     Rru I ----+--------+--------+--------+--------+--------+------°-
     Rsh I ----+--------+--------+----°---°+--------+--------+--------
     Sca I ----+--------+--------+--------+--------+--------+-----°--
     Xmn I ----+--------+--------+---°----+--------+--------+--------
     Xor II----+--------+--------+---°----°+--------+--------+--------
```

The specific makeup of the nucleotide bases of the gene of the present invention, and corresponding amino acids of the enzyme of the present invention into which they are translated, are shown, on a percentage basis, in the following table:

| | | | | | | | | | | | | | | | |
|---|---|---|---|---|---|---|---|---|---|---|---|---|---|---|---|
| TTT | Phe | 19 | 2.6% | TCT | Ser | 7 | 1.0% | TAT | Tyr | 25 | 3.5% | TGT | Cys | 2 | .3% |
| TTC | Phe | 8 | 1.1% | TCC | Ser | 3 | .4% | TAC | Tyr | 2 | .3% | TGC | Cys | 0 | .0% |
| TTA | Leu | 16 | 2.2% | TCA | Ser | 10 | 1.4% | TAA | — | 1 | — | TGA | — | 0 | — |
| TTG | Leu | 9 | 1.2% | TCG | Ser | 6 | .8% | TAG | — | 0 | — | TGG | Trp | 5 | .7% |
| CTT | Leu | 9 | 1.2% | CCT | Pro | 7 | 1.0% | CAT | His | 7 | 1.0% | CGT | Arg | 2 | .3% |
| CTC | Leu | 2 | .3% | CCC | Pro | 7 | 1.0% | CAC | His | 3 | .4% | CGC | Arg | 3 | .4% |
| CTA | Leu | 8 | 1.1% | CCA | Pro | 14 | 1.9% | CAA | Gln | 27 | 3.7% | CGA | Arg | 0 | .0% |

-continued

| | | | | | | | | | | | | | | | |
|---|---|---|---|---|---|---|---|---|---|---|---|---|---|---|---|
| CTG | Leu | 5 | .7% | CCG | Pro | 12 | 1.7% | CAG | Gln | 0 | .0% | CGG | Arg | 0 | .0% |
| ATT | Ile | 21 | 2.9% | ACT | Thr | 12 | 1.7% | AAT | Asn | 26 | 3.6% | AGT | Ser | 8 | 1.1% |
| ATC | Ile | 12 | 1.7% | ACC | Thr | 9 | 1.2% | AAC | Asn | 4 | .6% | AGC | Ser | 3 | .4% |
| ATA | Ile | 13 | 1.8% | ACA | Thr | 11 | 1.5% | AAA | Lys | 53 | 7.3% | AGA | Arg | 12 | 1.7% |
| ATG | Met | 27 | 3.7% | ACG | Thr | 13 | 1.8% | AAG | Lys | 15 | 2.1% | AGG | Arg | 2 | .3% |
| GTT | Val | 16 | 2.2% | GCT | Ala | 15 | 2.1% | GAT | Asp | 34 | 4.7% | GGT | Gly | 14 | 1.9% |
| GTC | Val | 7 | 1.0% | GCC | Ala | 8 | 1.1% | GAC | Asp | 5 | .7% | GGC | Gly | 11 | 1.5% |
| GTA | Val | 20 | 2.8% | GCA | Ala | 19 | 2.6% | GAA | Glu | 43 | 6.0% | GGA | Gly | 33 | 4.6% |
| GTG | Val | 11 | 1.5% | GCG | Ala | 7 | 1.0% | GAG | Glu | 14 | 1.9% | GGG | Gly | 6 | .8% |

It is also an object of the present invention to provide a method of producing the cephalosporin C amidase enzyme in improved yields by expressing it in a suitable prokaryotic or eukaryotic host, e.g., a Bacillus species, where said host has been transformed with a construction resulting from fusing of said gene to a promoter sequence, e.g., a strong constitutive promoter. The elements of this process are described in detail immediately below.

Site-Specific In Vitro Mutagenesis

Transformation of the prokaryotic or eukaryotic host with a construction comprising the gene encoding the cephalosporin C amidase fused to a promoter sequence, e.g., a strong constitutive promoter sequence, requires use of a vector. Regarding the preferred prokaryotic host, a Bacillus species, in order to facilitate vector construction, a BamHI site was introduced in front of the amidase coding sequences by site-specific in vitro mutagenesis in which a thymine (T) residue 29 base pairs upstream from the start of translation was converted to a cytosine (C) residue. This was accomplished by synthesizing the following oligonucleotide:

5' AATGATTATGGATCCATTGT 3'

This oligonucleotide was hybridized to the cephalosporin C amidase gene cloned into M13mp19 and a standard mutagenesis reaction was carried out of the type described in DNA 3:479–488 (1984). Mutants incorporating the appropriate base change were identified by the presence of a new BamHI site and confirmed by DNA sequencing. The altered sequence and its position relative to the cephalosporin C amidase structural gene is indicated below:

```
              -20           -10            +1
   •           •             •              •
AAACAATGGATCCATAATCATTTTGAAAGGAGACTAATTT ATG AAA TTT
       BamHI                                Met Lys Phe
```

Synthesis of the Strong Constitutive Promoter

A synthetic promoter based on the HpaII promoter of pUB110, as described in DNA 5:219–225 (1986), was synthesized in the following manner: two oligonucleotides (141 and 142, respectively) with the following sequences were synthesized:

5'-GGGGGATCCACAGCCTCGCATATCACACAC
TTTATGAATATAAAGTAT-3'
[oligonucleotide 141]

5'-GGGGATCCAACCACTTCCAAGTAAAGTATA
ACACATATACTTTATATTCATA-3'
[oligonucleotide 142]

The two oligonucleotides are complementary through the last 16 base pairs of each oligonucleotide. They were thus hybridized to each other and filled in with DNA polymerase 1 Klenow fragment and a mixture of deoxynucleotides. This generated a double stranded structure suitable for cloning by virtue of the BamHI site present at the 5' end of each oligonucleotide.

Other promoters which are suitable for expression of the cephalosporin C amidase gene in a Bacillus prokaryotic host can be synthesized and are contemplated to be a part of the present invention. For example, the following promoter was synthesized and designated 90/91:

5'-GAATTCACTTAAAAATTTCAGTTGCT
TAATCCTACAATTCTTGATATAATA
TTCTCATAGTTTGAAGGATCC-3'

This promoter has been reported in J. Mol. Biol., 186, 547–555 (1985) to be a strong Bacillus promoter and has been determined to be tenfold more active than the 141/142 promoter described above when driving expression of the chloramphenicol acetyl transferase gene.

Yet another suitable promoter has been found which is a natural *Bacillus megaterium* promoter and was isolated therefrom. It was found to have about fivefold better activity than the 141/142 promoter in driving the expression of the chloramphenicol acetyl transferase gene. Its base pair sequence is as follows:

5'-GCTTCCTTCGCATTTCCGTTCATCATTAAATA
GGGAGATAATCGCATTGTCATAATTAAATAG
CTCCTTTGGTTCTATTTTTTTTAACCAAAATC
TTTGAGTATCTTTCCAAGCTTCCTTTTTGAAA
CCTTGTCAGTGAATAAATAAACCACTATACC
ATTATTACCATGATTGTATTTTATAACAAGAA
CGTATGTTCGTCAATATATATCACTTGAAGAC
TAAACAATTTTCGATCCGGATTC-3'

Fusing of the Cephalosporin C Amidase Gene to the

Synthetic Strong Constitutive Promoter

The cephalosporin C amidase gene with the altered 5' sequence described above in the paragraph under "Site-Specific In Vitro Mutagenesis" and the synthetic strong constitutive promoter described in the paragraph immediately above were combined at the BamHI sites. A detailed description of this fusion product is shown in the paragraph immediately below, including the various promoter regions (A+T, −35, −10), the ribosome binding site (RBS), and the start of translation.

Construction of the Vector pCPC-1

The cephalosporin C amidase expression vector, labelled pCPC-1, was constructed by cloning the amidase gene fused to the strong constitutive promoter 141/142 into the Bacillus/E. coli shuttle vector pMK4 described in Gene 29:21-26 (1984).

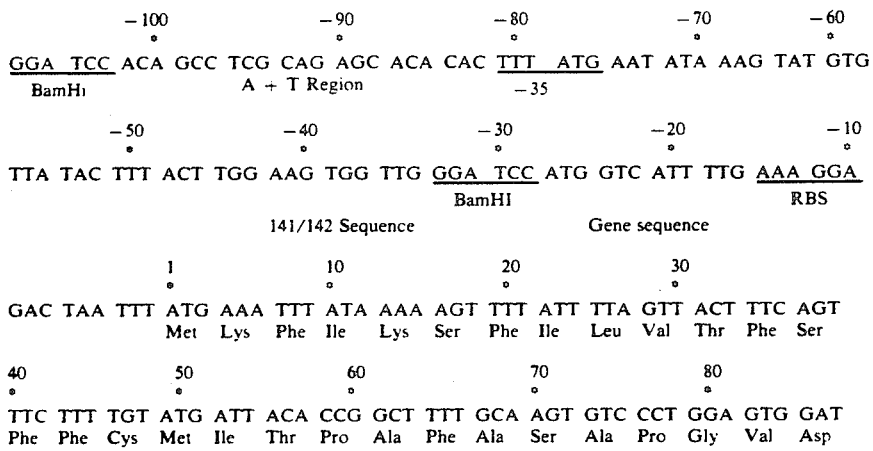

Expression of Cephalosporin C Amidase in *Bacillus subtilis* and *Bacillus megaterium*

The pCPC-1 vector described above was transformed into *B. subtilis* ATCC 39620 and *B. megaterium* NP-1 by standard methods, such as those described in Molec. Gen. Genet. 168, 111-115 (1979) and J. Bact. 142, 508-512 (1980). "NP-1" indicates a *B. megaterium* strain which produces little or no cephalosporin C amidase. Transformants and control cultures were grown overnight in LB media containing 10 μg/ml of chloramphenicol and used to inoculate cultures of fermentation media (FM) containing 10 μg/ml of chloramphenicol. These cultures were grown 3 to 4 days at 28° C. with shaking. Supernatants were concentrated 5 fold by ammonium sulfate precipitation (75% ammonium sulfate cut) and assayed for cephalosporin C amidase activity using cephalosporin C as substrate. The 200 μliter assay mixture contained 2 mg/ml cephalosporin C (final concentration) plus 180 μliters of 5× concentrated culture supernatant in 50 mM KHPO$_4$ (pH 7.5), 5% glycerol, and 15% NH$_4$SO$_4$. Liberation of 7-aminocephalosporanic acid (7-ACA) from cephalosporin C was assayed by HPLC.

*B. megaterium* NP-1 transformed with pCPC-1 liberated 157 μg of 7-ACA/ml of reaction mixture/3 hr assay time; whereas, control cultures of NP-1 liberated approximately 2 μg of 7-ACA. *B. subtilis* ATCC 39620 transformed with pCPC-1 liberated 0.52 μg of 7-ACA; whereas, control cultures of *B. subtilis* 39620 were negative.

Cephalosporin C amidase activity could also be detected in the overnight cultures grown in LB media when γ-glutamyl-p-aminobenzoic acid was used as the substrate for cephalosporin C amidase. *B. subtilis* 39620 transformed with pCPC-1 produced 2.7 units of activity (where 1 unit is defined as liberation of 1 nanomole of p-aminobenzoic acid (PABA)/minute/ml of culture supernatant); whereas, control cultures were negative. Using γ-glutamyl-p-aminobenzoic acid as substrate, the *B. megaterium* NP-1 transformed with pCPC-1 produced 3.5 units of amidase activity; whereas, control cultures were negative.

The Prokaryotic Host

As shown above, expression of the cephalosporin C amidase gene has been achieved in *Bacillus megaterium* and *Bacillus subtilis*. It is contemplated that, with use of a suitable promoter, expression of said gene can be obtained in any species of the Bacillus genus, and thus the present invention is directed to a method of expressing of said gene in a host comprising a member of the genus Bacillus.

It is also contemplated that with use of suitable promoter sequences and construction of suitable vectors containing constructs of the cephalosporin C amidase gene of the present invention fused to said promoter sequence, that it is possible to obtain expression of the gene in eukaryotic and other prokaryotic hosts, such as various species of Steptomyces, Saccharomyces, Aspergilus, Serratia, Cephalosporium, and Escherichia, among others.

In order to demonstrate the enzymatic deacylation of cephalosporin C to give 7-aminocephalosporanic acid (7-ACA), the general procedure illustrated below has been followed:

Enzyme preparation

Isolated colony from LB and chloramphenicol inoculate liquid LB media and chloramphenicol 18 hours at 37° C. inoculate production medium 60-96 hours at 30° C. harvest cell suspension and centrifuge to remove cells concentrate and partially purify activity by fractionation with (NH$_4$)$_2$SO$_4$ at 55-75% of saturation Assay of activity: incubate 180 μl enzyme with 20 μl 20 mg/ml cephalosporin C; after 3 hours at 37° determine 7-ACA by HPLC assay A more detailed description of the manner in which the enzyme of the present invention has been isolated and purified is set out immediately below.

Enzyme Purification

Cultures of *B. megaterium* were grown as described. The cells were removed from the broth by centrifugation. The broth was brought to 55% saturation with respect to ammonium sulfate and the precipitate removed by centrifugation. The supernatant was then brought to 75% saturated with respect to ammonium sulfate and the cephalosporin C amidase containing precipitate pelleted by centrifugation. This pellet was resuspended in 1/10 of the original culture volume of 15% (w/v) ammonium sulfate, 50 mM sodium phosphate, 5% (w/v) glycerol pH 7.5.

The 10× concentrated enzyme was brought from 15% to 18% w/v ammonium sulfate by addition of saturated ammonium sulfate and filtered through a 0.4 micron filter. Four mls of this was injected onto a Synchrome Synchropak propyl column (25 cm × 4.1 mM) which was previously equilibrated with 18% (w/v) ammonium sulfate, 50 mM potassium phosphate pH 7.0. The flow rate was 1 ml/min. For ten minutes after injection the mobile phase composition remained unchanged. From 10 to 40 minutes the mobile phase was changed in a linear gradient to 0% ammonium sulfate, 50 mM sodium phosphate pH 7. From 40–50 minutes the mobile phase composition remained unchanged. Two fractions/min. were collected and assayed for cephalosporin C amidase activity. The activity eluted from 22 to 25 minutes.

The five fractions with the most activity were pooled and concentrated by ultrafiltration in a Centricon 30 (Amicon) to about 50 μl. This concentrated enzyme was injected onto a Zorbox GF 250 (DuPont) column (250 mM × 9.4 mM). The column had been equilibrated and was run in 10% (w/v) ammonium sulfate, 50 mM potassium phosphate pH 7.0 at 1 ml/min. Five fractions/min. were collected. All of the cephalosporin C amidase activity was recovered in two fractions at approximately 9 minutes after injection.

Sodium dodecyl sulfate gel electrophoresis of these active fractions showed the cephalosporin C amidase to be approximately 99% of the total coomasie stained protein.

As illustrated in more particular detail below, the general procedure described above were followed in the working examples:

EXAMPLE 1

Preparation and Assay of Cephalosporin C Amidase Activity from Cultures of *Bacillus megaterium*

Culture Conditions

1. The strains were maintained on LB agar plates (supplemented with 10 μg/ml chloramphenicol) of the following composition:

| COMPONENT | g/l |
| --- | --- |
| tryptone | 10 |
| yeast extract | 5 |
| NaCl | 5 |
| agar | 15 |

2. Reisolated colonies were obtained by streaking on LB plus chloramphenicol plates followed by overnight incubation at 37° C. Isolated colonies were used to inoculate 5 ml of LB plus chloramphenicol liquid media, which is identical to the media listed above, except that it lacks the agar component. These culture were incubated overnight at 37° C.

3. The 5 ml overnight cultures were used to inoculate 40 ml cultures of fermentation media (FM) supplemented with 10 μg/ml chloramphenicol. FM is of the following composition:

| COMPONENT | g/l |
| --- | --- |
| beef extract | 4.5 |
| casitone | 9.0 |
| soybean meal | 15.0 |
| dextrose | 5.0 |
| soluble starch | 30 |
| lactose | 30 |

4. The cultures in FM were incubated at 30° C. on a rotary shaker (220 rpm) for 3–4 days, until the pH of the culture was 8.0 or above.

Enzyme Recovery

1. Cells were removed from the cultures by centrifugation at 10,000 rpm for 10 minutes.

2. To 2.5 ml of the above centrifuged supernatant was added 7.5 ml of saturated ammonium sulfate, followed by 10 minutes on ice and centrifugation at 10,000 rpm for 10 minutes. The pellets were resuspended in 0.5 ml of high salt buffer (HSB) for assay with cephalosporin C as substrate. HSB is of the following composition:

| HSB |
| --- |
| 50 mM KHPO$_4$, pH 7.5 |
| 5% glycerol |
| 15% NH$_4$SO$_4$ |

Enzyme Assay

1. The substrate stock solution was prepared by dissolving 20 mg of cephalosporin C in 1 ml of water.

2. Cephalosporin C stock solution (20 μl) was added to the recovered enzyme (180 μl) and the mixture was incubated at 37° C. for 3 hours. Formation of 7-ACA was monitored by HPLC. The following HPLC conditions were used:

| | |
| --- | --- |
| mobile phase | 50 mM KH$_2$PO$_4$ |
| flow rate | 2.0 ml/min |
| column | Waters Novapak C18, 0.4 × 10 cm |
| temperature | ambient |
| detector | 254 nm |
| sample size | 20 μl |
| instrument | Waters |

Retention time of the 7-ACA was ca. 5.0 minutes under these conditions.

Activity Assay Results

1. Following processing as described above, the enzyme preparation produced 157 μg of 7-ACA per ml of reaction mixture per 3 hour incubation in the presence of 2 mg/ml cephalosporin C.

EXAMPLE 2

One-step Enzymatic Conversion of Cephalosporin C to 7-Aminocephalosporanic Acid: Direct Measurement of the Cleavage Products In order to provide further evidence that the conversion of cephalosporin C to 7-aminocephalosporanic acid (7-ACA) in accordance with the present invention is indeed a one-step process accomplished by a single enzyme, (cephalosporin C amidase), cleavage is carried out as described above in Example 1; but in addition to measuring formation of 7-ACA by HPLC as described in Example 1, the appearance of the other cleavage product, aminoadipic acid, is measured as well. This is done using a Beckman 6300 High Performance Analyzer. The enzyme is incubated with cephalosporin C (2 mg/ml final concentration) for 2.8 hours at 37° C. The one to one molar ratio of isolated products is good evidence for a one-step conversion of cephalosporin C to 7-ACA by the amidase enzyme.

What is claimed is:

1. An isolated enzyme, cephalosporin C amidase, produced by culturing a *Bacillus megaterium* strain in a nutrient medium containing assimilable sources of carbon, nitrogen and inorganic substances, comprising the following primary translation product amino acid sequence or a post-translational modification thereof or fragments thereof which are enzymatically active as a one-step cephalosporin C amidase:

```
  1  MKFIKSFILV TFSFFCMITP AFASVPGVDK
     SMGRGATKGI VSVSHPLAAE AGIKILKQGG

61  NAVDAAAAIQ LSLNVVEPMM SGIGGGGFIM
     IYNKKENKIT MLDSREMAPQ NVTPELFLDG

121  KGKPIPFSKR HTTGKAVGVP GTLKGVETAL
     EKYGTLDISQ VIDPAIKQAE KGVKVNWITA

181  QYIDENVKKL QNNQAAANVF VPNGQPLKEG
     DTLVQPDLAK TLKLIKKQGS EVFYSGQIGK

241  ALTKEVQKRE GTMTTEDLEN YVVKEREPIR
```

-continued
```
     SEYRGYELAG AASPSSGSLT VQQILELMEG

301  FDVQKMGANS PEYLHYLTEA MHLAFADRAA
     YMADEDFYDV PTKGLLDEDY IKERRKIINP

361  NRSTADVKEG DPWKYEGTEP TSMKKVKEEK
     TPIGQTTHFS VMDKWGNMVA YTTTIEQVFG

421  SGIMVPDYGF MLNNEMTDFD ATPGGVNQVE
     PGKRPRSSMS PTFVLKDGNP FMAIGSPGGA

481  TIIASVSETI MNVLDHQMLI QDAILAPRIY
     SAGYPTVRWE PGIEQNTRLE LMGKGHVYEE

541  KPQHIGNVQA VIFDYEKGKM YGGADNTREG
     TVQGVYNVSY KSKKPKEIKE EKKGPFTLKV

601  NGAVYPYTAE QMKLINEKPY IQSDKLLLGL
     GVIGTGDLET FRPDKKSYLP VIKVAKSLGY

661  KAKWNEKDKE ALLEKDPADI EDPEDDGSVT
     IIFHSKFKFH MVDNTLRDEE FEVIVVLTLN

721  EC
```

* * * * *